(12) United States Patent
Gu et al.

(10) Patent No.: US 11,607,193 B2
(45) Date of Patent: Mar. 21, 2023

(54) ULTRASONIC PROBE

(71) Applicant: SAMSUNG MEDISON CO., LTD., Gangwon-do (KR)

(72) Inventors: Jin Ho Gu, Seongnam-si (KR); Gil Ju Jin, Seoul (KR); Dong Hyun Kim, Suwon-si (KR); Jae Yk Kim, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 876 days.

(21) Appl. No.: 16/248,072

(22) Filed: Jan. 15, 2019

(65) Prior Publication Data
US 2019/0216428 A1    Jul. 18, 2019

(30) Foreign Application Priority Data
Jan. 15, 2018    (KR) .................. 10-2018-0005035

(51) Int. Cl.
*A61B 8/00*    (2006.01)
*G10K 11/30*    (2006.01)

(52) U.S. Cl.
CPC .......... *A61B 8/4455* (2013.01); *A61B 8/4272* (2013.01); *A61B 8/4405* (2013.01); *A61B 8/4422* (2013.01); *A61B 8/4494* (2013.01); *G10K 11/30* (2013.01)

(58) Field of Classification Search
CPC ... A61B 8/4272; A61B 8/4405; A61B 8/4422; A61B 8/4455; A61B 8/4494; G10K 11/30
See application file for complete search history.

(56) References Cited

U.S. PATENT DOCUMENTS

| 11,406,358 B2 | 8/2022 | Kwon et al. |
| 2014/0211587 A1 | 7/2014 | Kiyose |
| 2015/0266059 A1 | 9/2015 | Kubo et al. |
| 2016/0151044 A1 | 6/2016 | Kim et al. |
| 2019/0059853 A1 | 2/2019 | Kwon et al. |

FOREIGN PATENT DOCUMENTS

| JP | 2009-034212 A | 2/2009 |
| JP | 2009-142555 A | 7/2009 |
| KR | 10-2017-0098474 A | 8/2017 |
| WO | 2013/191060 A1 | 12/2013 |
| WO | 2014/092472 A1 | 6/2014 |
| WO | 2017/146364 A1 | 8/2017 |

OTHER PUBLICATIONS

Extended Search Report issued in corrsponding European Application No. 19151794.5, dated May 17, 2019.
Korean Office Action dated Feb. 3, 2023 issued in Korean Patent Application No. 10-2018-0005035 (with English translation).

*Primary Examiner* — Michael T Rozanski
(74) *Attorney, Agent, or Firm* — Morgan, Lewis & Bockius LLP

(57) ABSTRACT

An ultrasonic probe for acquiring an ultrasonic image is provided. The ultrasonic probe includes a transducer generating an ultrasonic signal and including a lens provided to transmit the ultrasonic signal to the outside, a case accommodating the transducer and having an opening at one side so that the lens is brought into contact with an external target object, and a buffer member provided along a circumference of the transducer to protect the transducer from external impact and disposed between the case and the transducer.

18 Claims, 12 Drawing Sheets

ULTRASONIC PROBE

CROSS-REFERENCE TO RELATED APPLICATION(S)

This application is based on and claims priority under 35 U.S.C. § 119 to Korean Patent Application No. 10-2018-0005035, filed on Jan. 15, 2018 in the Korean Intellectual Property Office, the disclosure of which is incorporated by reference herein in its entirety.

BACKGROUND

1. Technical Field

The present disclosure relates to an ultrasonic probe for acquiring an ultrasonic image.

2. Description of the Related Art

An ultrasonic imaging apparatus is an apparatus that irradiates an ultrasonic signal from a body surface of a target toward a target site in the body and obtains an image of a monolayer or blood flow of soft tissue without invasion by using information of a reflected ultrasonic signal (ultrasonic echo signal).

The ultrasonic imaging apparatus is small, inexpensive, real-time displayable, easy to use, and has high safety because there is no radiation exposure, compared to other imaging apparatuses such as an X-ray diagnostic apparatus, an X-ray CT scanner, an MRI (Magnetic Resonance Image) and a nuclear medicine diagnostic apparatus.

Therefore, the ultrasonic imaging apparatus has been widely used for the diagnosis of the heart, abdomen, urinary system and obstetrics.

Generally, the ultrasonic imaging apparatus may include a main body and an ultrasonic probe that transmits ultrasonic signals to a target object to be diagnosed and receives signals reflected from the target object.

The ultrasonic probe may have a structure in which an ultrasonic signal transmitted from an internal piezoelectric layer is transmitted to a target object through a lens provided so as to come into contact with the target object and an ultrasonic signal reflected back from the target object is received again through the lens.

Since the lens of the ultrasonic probe is exposed to the outside and is configured to have a very thin thickness, when the ultrasonic probe is used by a user, the possibility of breakage or damage of the ultrasonic probe may be increased due to the ultrasonic probe being dropped due to carelessness of the user.

Generally, since a separate safety device for preventing the ultrasonic probe from dropping is not provided in the process of manufacturing the ultrasonic probe, it is necessary to add rubber or the like to a handle of the ultrasonic probe to increase a frictional force between the handle and the user's hand in order to protect the ultrasonic probe from external impact.

However, the method of adding rubber or the like to the handle is not preferable for hygiene, causes an additional purchase cost, and may reduce the satisfaction of the user in a situation where promptness of diagnosis is important.

Therefore, a separate shock-absorbing device for protecting a transducer including the lens from external shock may be required.

SUMMARY

It is an aspect of the present disclosure to provide an improved ultrasonic probe to prevent a transducer from being damaged by external impact.

It is another aspect of the present disclosure to provide an improved ultrasonic probe to prevent a lens and a piezoelectric layer from being damaged by external impact.

It is another aspect of the present disclosure to provide an improved ultrasonic probe to include a buffer member disposed around a transducer.

Additional aspects of the present disclosure will be set forth in part in the description which follows and, in part, will be obvious from the description, or may be learned by practice of the disclosure.

In accordance with an aspect of the present disclosure, an ultrasonic probe may include a transducer generating an ultrasonic signal and including a lens provided to transmit the ultrasonic signal to the outside, a case accommodating the transducer and having an opening at one side so that the lens is brought into contact with an external target object, and a buffer member provided along a circumference of the transducer to protect the transducer from external impact and disposed between the case and the transducer.

The transducer may further include a piezoelectric layer positioned adjacent to the lens and provided to generate the ultrasonic signal, and the buffer member may be disposed between the case and the piezoelectric layer.

The buffer member may be provided along a circumference of the piezoelectric layer to cover the piezoelectric layer.

The buffer member may be provided to cover entire side surfaces of the piezoelectric layer.

The hardness of the buffer member may be lesser than the hardness of the case and greater than the hardness of the lens.

The elasticity of the buffer member may be higher than the elasticity of the case.

The buffer member may include a first buffer part provided along a circumference of the transducer and a second buffer part provided on a portion of the first buffer part.

The buffer member may include a buffer space provided inside the buffer member and a buffer membrane provided to cover the buffer space.

The buffer space may be filled with a material different from the material of the buffer membrane.

The buffer space may be filled with a fluid.

A plurality of the second buffer parts may be provided, and the first buffer part may include a first cushion portion provided between the plurality of second buffer parts and a first pressure portion disposed adjacent to the first cushion portion.

The volume of the first cushion portion may be larger than the volume of the first pressure portion.

A plurality of the first cushion portions and a plurality of the first pressure portions may be provided, and the plurality of first cushion portions and the plurality of first pressure portions may be alternately arranged.

The second buffer part may include a second cushion portion having a larger volume than the volume of the first buffer part, and a second pressure portion disposed between the first buffer part and the second cushion portion.

The volume of the second pressure portion may be smaller than the volume of the second cushion portion.

In accordance with another aspect of the present disclosure, an ultrasonic probe may include a case, a transducer accommodated inside the case, and including a piezoelectric layer for generating an ultrasonic signal and a lens disposed adjacent to the piezoelectric layer and provided to transmit the ultrasonic signal to the outside, and a buffer member provided along a circumference of the piezoelectric layer to protect the piezoelectric layer from external impact and disposed between the case and the piezoelectric layer.

The buffer member may include a first buffer part provided to cover entire side surfaces of the transducer and a second buffer part provided on a portion of the first buffer part.

The buffer member may include a buffer space provided inside the buffer member and a buffer membrane provided to cover the buffer space.

In accordance with another aspect of the present disclosure, an ultrasonic probe may include a case, a handle connected to one side of the case, a transducer accommodated inside the case to generate an ultrasonic signal and including a lens provided to transmit the ultrasonic signal to the outside, a first buffer part provided along a side surface of the transducer to form a loop, and a second buffer part disposed between the case and the transducer, the second buffer part being provided on a portion of the first buffer part.

The first buffer part may include a first cushion portion positioned between the lens and the handle, and a first pressure portion disposed adjacent to the first cushion portion and having a volume smaller than a volume of the first cushion portion, and the second buffer part may include a second cushion portion positioned between the first buffer part and the handle, and a second pressure portion disposed adjacent to the second cushion portion and having a volume smaller than a volume of the second cushion portion.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
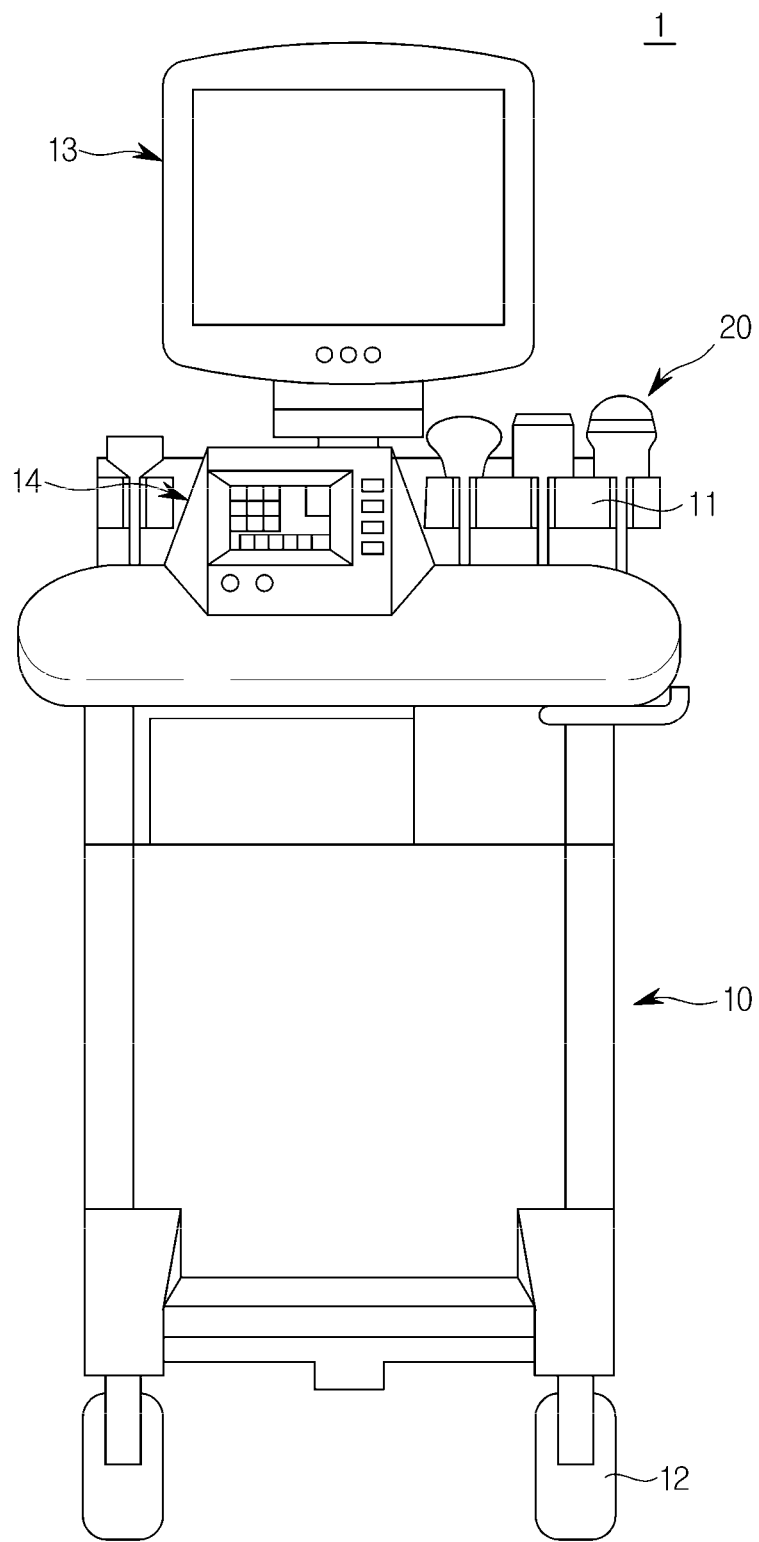
FIG. 1 is a view illustrating an ultrasonic imaging apparatus including an ultrasonic probe according to the present disclosure.

The embodiments described herein and the configurations shown in the drawings are only examples of preferred embodiments of the present disclosure, and various modifications may be made at the time of filing of the present disclosure to replace the embodiments and drawings of the present disclosure.

Like reference numbers or designations in the drawings of the present disclosure represent parts or components that perform substantially the same functions.

The terms used in the present disclosure are for the purpose of describing the embodiments and are not intended to restrict and/or to limit the disclosure. For example, the singular expressions herein may include plural expressions, unless the context clearly dictates otherwise.

The terms "comprises" and "has" are intended to indicate that there are features, numbers, steps, operations, elements, parts, or combinations thereof described in the present specification, and do not exclude the presence or addition of one or more other features, numbers, steps, operations, elements, parts, or combinations thereof.

It will be understood that, although the terms first, second, etc. may be used herein to describe various components, these components should not be limited by these terms. These terms are only used to distinguish one component from another. For example, without departing from the scope of the present disclosure, the first component may be referred to as a second component, and similarly, the second component may also be referred to as a first component.

The term "and/or" includes any combination of a plurality of related items or any one of a plurality of related items.

In this specification, the terms "front," "rear," "upper," "lower," "left," and "right" are defined with reference to the drawings, and the shape and position of each component are not limited by these terms.

Hereinafter, embodiments according to the present disclosure will be described in detail with reference to the accompanying drawings.

FIG. 1 is a view illustrating an ultrasonic imaging apparatus including an ultrasonic probe according to the present disclosure. Referring to FIG. 1, an ultrasonic imaging apparatus 1 according to the present disclosure may include a main body 10, and an ultrasonic probe 20 to transmit ultrasonic signals to a target object to be diagnosed and receive signals reflected from the target object.

The ultrasonic probe 20 may transmit an ultrasonic signal to a target object to obtain an ultrasonic image of the target object, receive the ultrasonic signal reflected from the target object, and transmit the reflected ultrasonic signal to a controller (not shown). The ultrasonic probe 20 may be connected to the main body 10 by a cable.

The main body 10 may be provided with a display 13 to display a diagnosis result obtained through the received ultrasonic signal. An application related to the operation of the ultrasonic imaging apparatus 1 may be displayed on the display 13.

As an example, the display 13 may display an ultrasonic image obtained in an ultrasonic diagnostic process or items related to the operation of the ultrasonic imaging apparatus 1.

The display 13 may be implemented as a cathode ray tube (CRT), a liquid crystal display (LCD), or the like. A plurality of the displays 13 may be provided. In a case where the plurality of displays 13 are provided, the displays 13 may include a main display and a secondary display.

As an example, the ultrasonic image obtained in an ultrasonic diagnostic process may be displayed on the main display, and items related to the operation of the ultrasonic imaging apparatus 1 may be displayed on the secondary display.

The main body 10 may be provided with an input 14. The input 14 may be provided in the form of a keyboard, a foot switch, a foot pedal, or the like.

In a case where the input 14 is a keyboard, it may be provided at an upper portion of the main body 10. In a case where the input 14 is a foot switch or a foot pedal, it may be provided at a lower portion of the main body 10. An inspector may control the operation of the ultrasonic imaging apparatus 1 through the input 14.

The ultrasonic probe 20 may be mounted on the main body 10 by a holder 11. When the ultrasonic imaging apparatus 1 is not used, the inspector may mount the ultrasonic probe 20 on the holder 11 and store it in the holder 11.

The main body 10 may be provided with a moving device 12 to move the ultrasonic imaging apparatus 1. The moving device 12 may be a plurality of casters provided on the bottom surface of the main body 10.

The plurality of casters may be aligned to allow the main body 10 to travel in a specific direction, may be provided to be freely movable in any direction, or may be locked to stop at a specific position.

Figure 2:
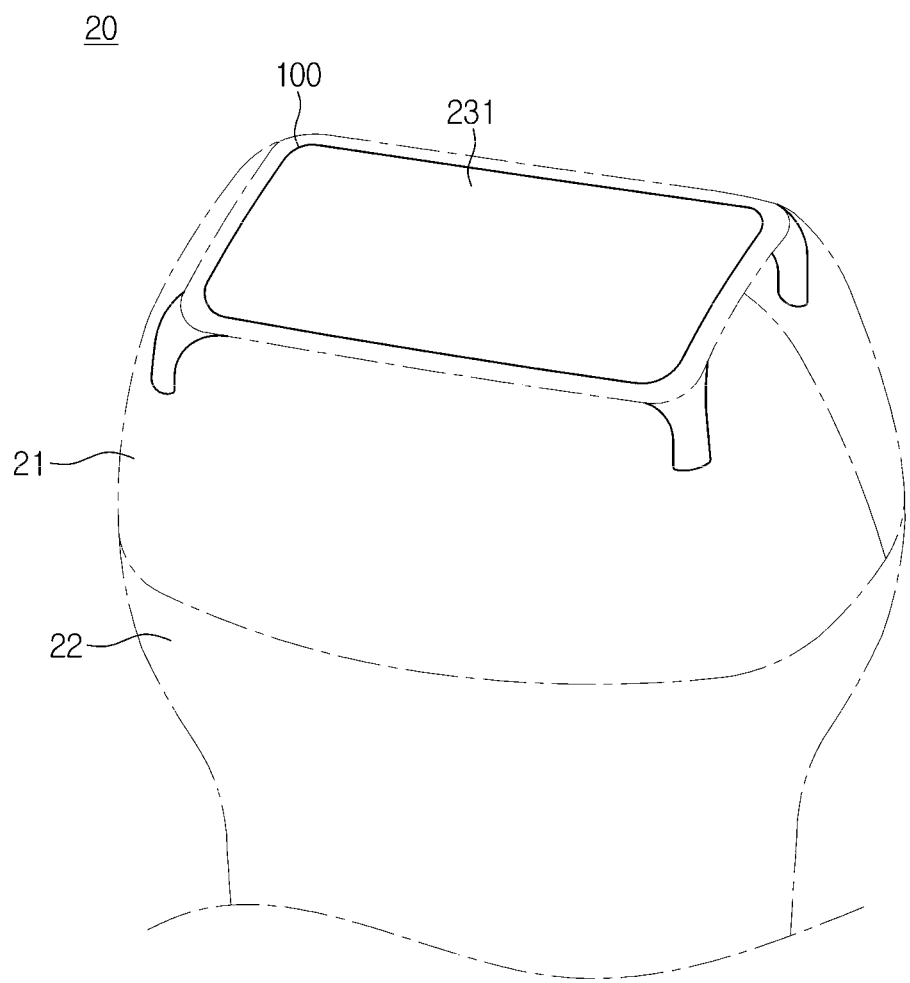
FIG. 2 is a view illustrating an ultrasonic probe according to an embodiment of the present disclosure.
Figure 3:
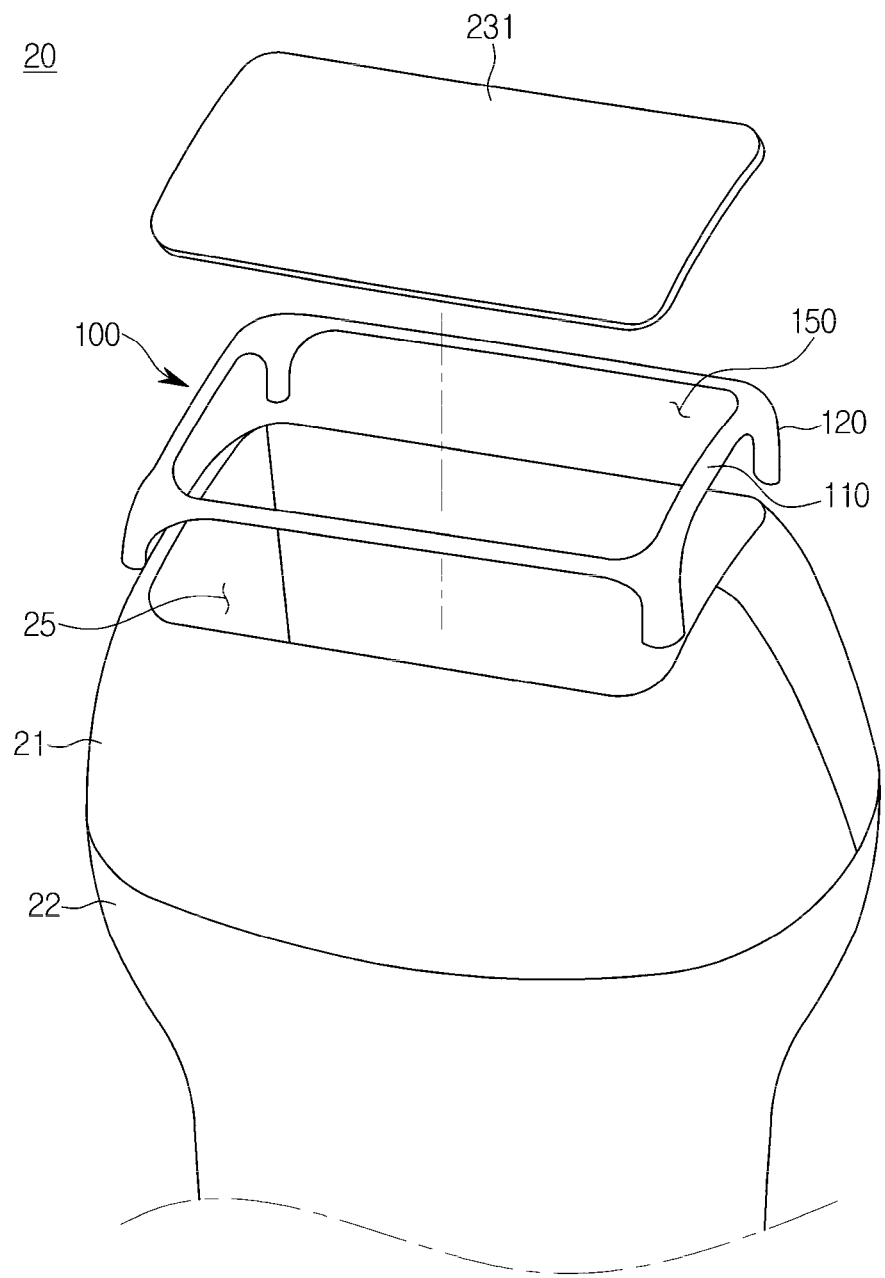
FIG. 3 is an exploded view of a lens and a buffer member in an ultrasonic probe according to an embodiment of the present disclosure.
Figure 4:
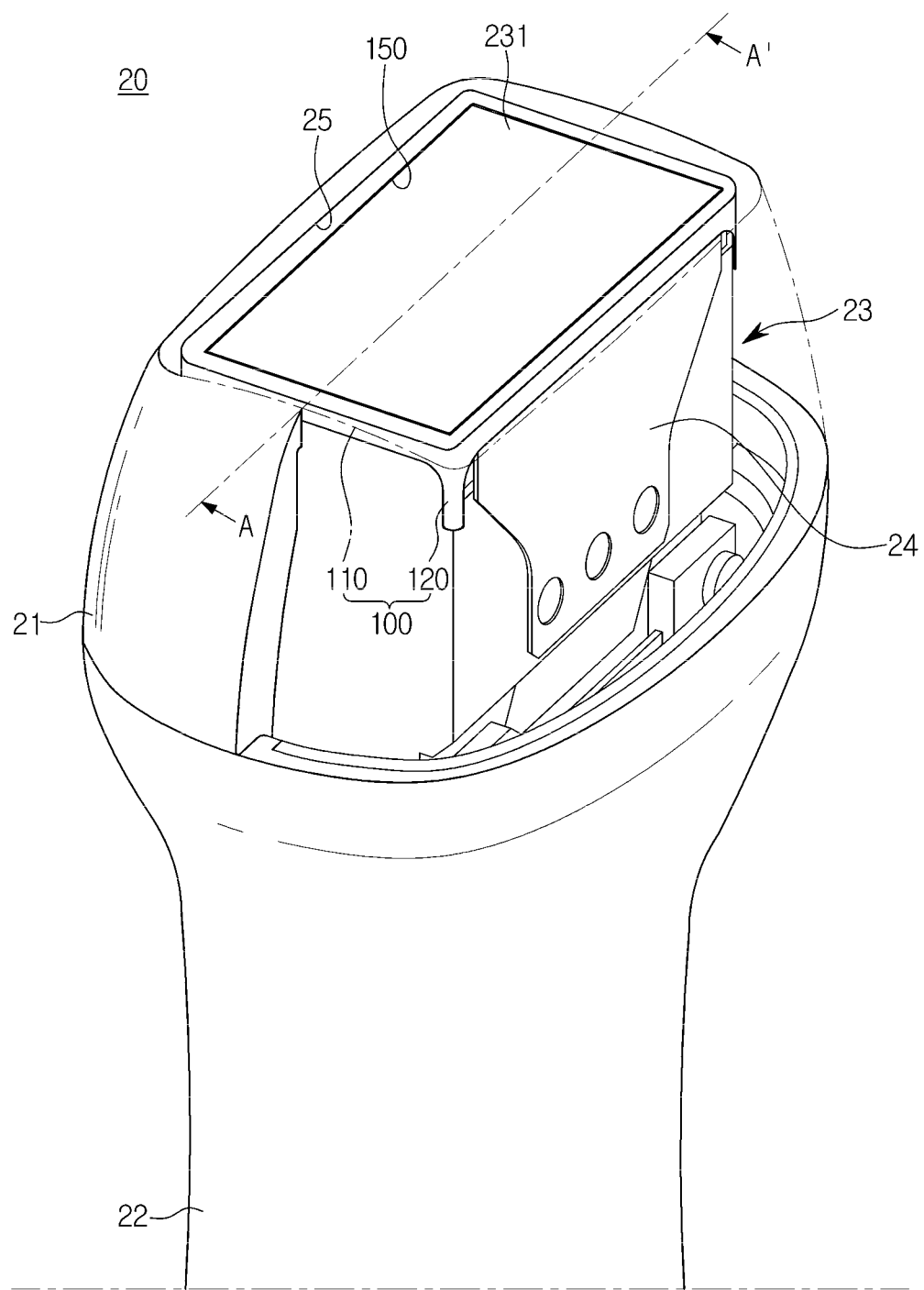
FIG. 4 is a view schematically illustrating the inside of an ultrasonic probe according to an embodiment of the present disclosure.

FIG. 2 is a view illustrating an ultrasonic probe according to an embodiment of the present disclosure, FIG. 3 is an exploded view of a lens and a buffer member in an ultrasonic probe according to an embodiment of the present disclosure, and FIG. 4 is a view schematically illustrating the inside of an ultrasonic probe according to an embodiment of the present disclosure.

As illustrated in FIGS. 2 to 4, the ultrasonic probe 20 may include a transducer 23 that generates an ultrasonic signal and includes a lens 231 provided to transmit the ultrasonic signal to the outside. The lens 231 may focus the ultrasonic signal.

The ultrasonic probe 20 may include a case 21 that accommodates the transducer 23 and has an opening 25 at one side so that the lens 231 is brought into contact with an external target object, and a handle 22 mounted on the other side of the case 21.

The lens 231 may be provided with a material such as silicon, rubber, or the like having an acoustic impedance value similar to the acoustic impedance of the target object. The lens 231 may be a convex type having a convex curved surface at the center or may be a linear type having a flat surface.

The transducer 23 may include a substrate 24 provided to transmit an electrical signal to the transducer 23. The substrate 24 may include a flexible printed circuit board.

A buffer member 100 capable of protecting the transducer 23 from external impact may be provided in the case 21. The buffer member 100 may be provided on one side of the transducer 23.

The buffer member 100 may be disposed between the case 21 and the transducer 23. The buffer member 100 may be provided along a circumference of the transducer 23. The buffer member 100 may be disposed to surround a side surface of the transducer 23. The buffer member 100 may be provided to cover the entirety of the side surfaces of the transducer 23.

Herein, the circumference of the transducer 23 refers to a rim or outer edge of the transducer 23 and may include a portion of the rim of the transducer 23 or the entire rim of the transducer 23.

That is, the buffer member 100 according to the present disclosure may be disposed along at least a portion of the circumference of the transducer 23. The buffer member 100 may also be disposed along the entire circumference of the transducer 23.

The buffer member 100 may be provided so as to form a loop along the side surface of the transducer 23, but is not limited thereto.

The transducer 23 is protected by the buffer member 100 so that the external impact applied to the ultrasonic probe 20 may not be directly transmitted to the transducer 23.

In a case where a user drops the ultrasonic probe 20 or the ultrasonic probe 20 strongly collides with another object while the user holds the handle 22 and uses the ultrasonic probe 20, the transducer 23 located inside the ultrasonic probe 20 may be damaged by external impact.

In particular, since the lens 231 positioned in front of the transducer 23 may be provided with a soft material including silicone, rubber, etc., the lens 231 may not protect the transducer 23 located inside the ultrasonic probe 20 from external impact.

Accordingly, the ultrasonic probe 20 may be more vulnerable to external impact transmitted through a front surface of the ultrasonic probe 20 in which the lens 231 is positioned or the corner portions where the case 21 and the lens 231 are connected.

Since the ultrasonic probe 20 according to the present disclosure is provided with the buffer member 100 between the side surfaces of the case 21 and the transducer 23, external impact applied to the front surface or side edges of the ultrasonic probe 20 may not be transmitted to the transducer 23 by the buffer member 100 or the external impact may be buffered by the buffer member 100 and transmitted to the transducer 23.

That is, the external impact may be first transferred to the buffer member 100, and buffered in the buffer member 100 and then transferred to the transducer 23. Therefore, the transducer 23 may be prevented from being damaged due to the external impact by the buffer member 100.

The hardness of the buffer member 100 may be lesser than the hardness of the case 21. The hardness of the buffer member 100 may be greater than the hardness of the lens 231. The elasticity of the buffer member 100 may be higher than the elasticity of the case 21. However, the present disclosure is not limited thereto.

The buffer member 100 may include a first buffer part 110 provided along the circumference of the transducer 23 and a second buffer part 120 provided on a portion of the first buffer part 110.

The first buffer part 110 may be looped to cover entire side surfaces of the transducer 23. The second buffer part 120 may be disposed at a position where an edge of the first buffer part 110 meets. The second buffer part 120 may extend in a direction from the first buffer part 110 toward the handle 22.

The second buffer part 120 may be disposed in the rear of the first buffer part 110. A plurality of the second buffer parts 120 may be provided. In a case where the first buffer part 110 has a substantially rectangular ring shape, the second buffer parts 120 may be positioned at each corner of the first buffer part 110, but are not limited thereto.

The buffer member 100 may include a hole 150 through which the transducer 23 including the lens 231 passes. The lens 231 may be brought into contact with an external target object through the opening 25 of the case 21 and the hole 150 of the buffer member 100.

Figure 5:
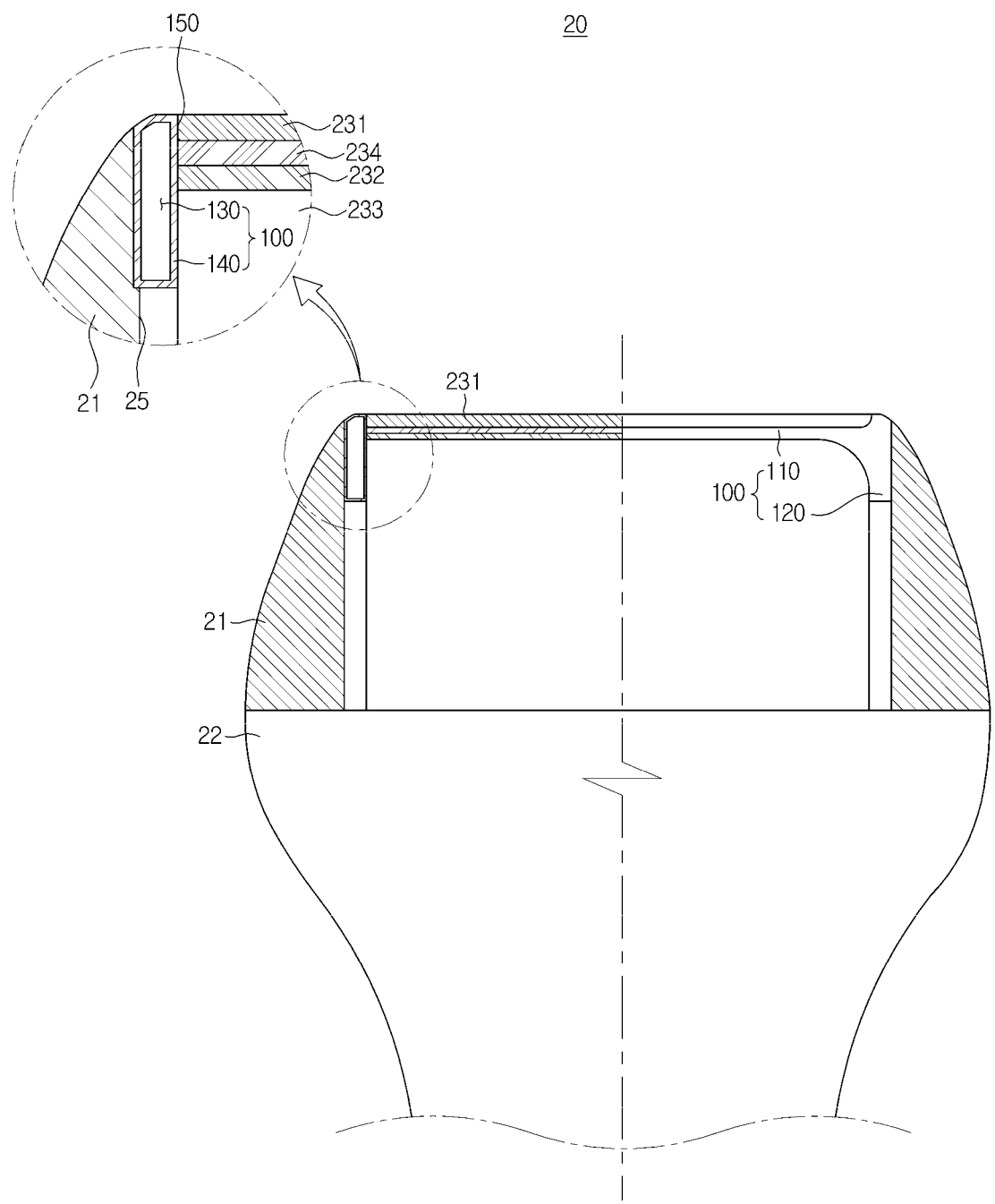
FIG. 5 is a cross-sectional view taken along line A-A' of the ultrasonic probe according to the embodiment of the present disclosure illustrated in FIG. 4.

FIG. 5 is a cross-sectional view taken along line A-A' of the ultrasonic probe according to the embodiment of the present disclosure illustrated in FIG. 4. As illustrated in FIG. 5, the transducer 23 (refer to FIG. 4) provided in the ultrasonic probe 20 may include a piezoelectric layer 232 for converting an electric signal into an acoustic signal while the piezoelectric material vibrates.

The piezoelectric layer 232, which is configured to generate ultrasonic waves using a resonance phenomenon, may be formed of a PZNT single crystal made of a solid solution of zirconate titanate (PZT) ceramic, zinc niobate and titanium oxide, and a PZMT single crystal made of a solid solution of magnesium niobate and titanate.

Electrodes (not shown) corresponding to a positive electrode and a negative electrode may be provided on a front side and a rear side of the piezoelectric layer 232, respectively. The electrodes may be comprised of a highly conductive metal such as gold, silver or copper, and the electrode corresponding to the positive electrode and the electrode corresponding to the negative electrode may be electrically connected to the substrate 24 (refer to FIG. 4) to receive electricity.

The transducer 23 may include a sound-absorbing layer 233. The sound-absorbing layer 233 may be disposed adjacent to the piezoelectric layer 232. The sound-absorbing layer 233 may be positioned in the rear of the piezoelectric layer 232.

The sound-absorbing layer 233 may suppress the free vibration of the piezoelectric layer 232 to reduce the pulse width of the ultrasonic waves, and may prevent the ultrasonic image from being distorted by blocking the ultrasonic wave from being unnecessarily propagated to the rear side of the piezoelectric layer 232.

The sound-absorbing layer 233 may be made of a material including rubber added with epoxy resin, tungsten powder, or the like.

The transducer 23 may comprise an acoustic matching layer 234. The acoustic matching layer 234 may reduce the acoustic impedance difference between the piezoelectric layer 232 and the target object so that the ultrasonic waves generated in the piezoelectric layer 232 are transmitted to the target object as much as possible.

The acoustic matching layer 234 may be disposed adjacent to the piezoelectric layer 232. The acoustic matching layer 234 may be positioned in front of the piezoelectric layer 232. The acoustic matching layer 234 may be provided to have an intermediate value between the acoustic impedance of the piezoelectric layer 232 and the acoustic impedance of the object, and may be formed of glass or a resin material.

The acoustic matching layer 234 may be formed by stacking a plurality of the acoustic matching layers 234 having different materials so that the acoustic impedance may gradually change from the piezoelectric layer 232 toward the target object.

On the other hand, the piezoelectric layer 232 may be provided in the form of an air kerf to maximize the ultrasonic generation performance. Such a piezoelectric layer 232 in the form of an air kerf may be more vulnerable to external impact.

Therefore, when the piezoelectric layer 232 in the form of an air kerf is provided, the transducer 23 may be more easily damaged by external impact.

The buffer member 100 according to the present disclosure may be provided between the case 21 and the piezoelectric layer 232. The buffer member 100 may be provided along a circumference of the piezoelectric layer 232 to cover the piezoelectric layer 232. The buffer member 100 may be provided to cover entire side surfaces of the piezoelectric layer 232.

The first buffer part 110 may be looped to cover the entire side surfaces of the piezoelectric layer 232. The second buffer part 120 may be disposed on a portion of the first buffer part 110 to cover side surfaces of the piezoelectric layer 232.

As the buffer member 100 is provided to cover the side surfaces of the piezoelectric layer 232, the external impact to be transmitted to the piezoelectric layer 232 may be transmitted to the buffer member 100 first.

Accordingly, the piezoelectric layer 232 may be protected from external impact by the buffer member 100. Particularly, the external impact transmitted through the edge portion of the ultrasonic probe 20 may be prevented from being transmitted to the piezoelectric layer 232 by the buffer member 100.

The buffer member 100 according to the present disclosure may be provided along the circumference of the transducer 23 so as to cover the sound-absorbing layer 233, the acoustic matching layer 234 or the lens 231 in addition to the piezoelectric layer 232.

The first buffer part 110 may be looped to cover entire side surfaces of the sound-absorbing layer 233, the acoustic matching layer 234, or the lens 231. The second buffer part 120 may be disposed on a portion of the first buffer part 110 so as to cover the side surfaces of the sound-absorbing layer 233, the acoustic matching layer 234 or the lens 231, but is not limited thereto.

Accordingly, the ultrasonic probe 20 according to the present disclosure may buffer external impact transmitted to the transducer 23 by the buffer member 100.

The buffer member 100 may include a buffer space 130 provided in the buffer member 100 and a buffer membrane 140 provided to cover the buffer space 130.

The buffer membrane 140 may firstly buffer external impact. The buffer space 130 may secondarily buffer the impact that has firstly been buffered by the buffer membrane 140.

The buffer space 130 may be filled with a material different from that of the buffer membrane 140, but is not limited thereto. That is, the buffer space 130 may be filled with the same material as that of the buffer membrane 140.

The buffer space 130 may be filled with a fluid such as air, oil, and alcohol.

Figure 6:
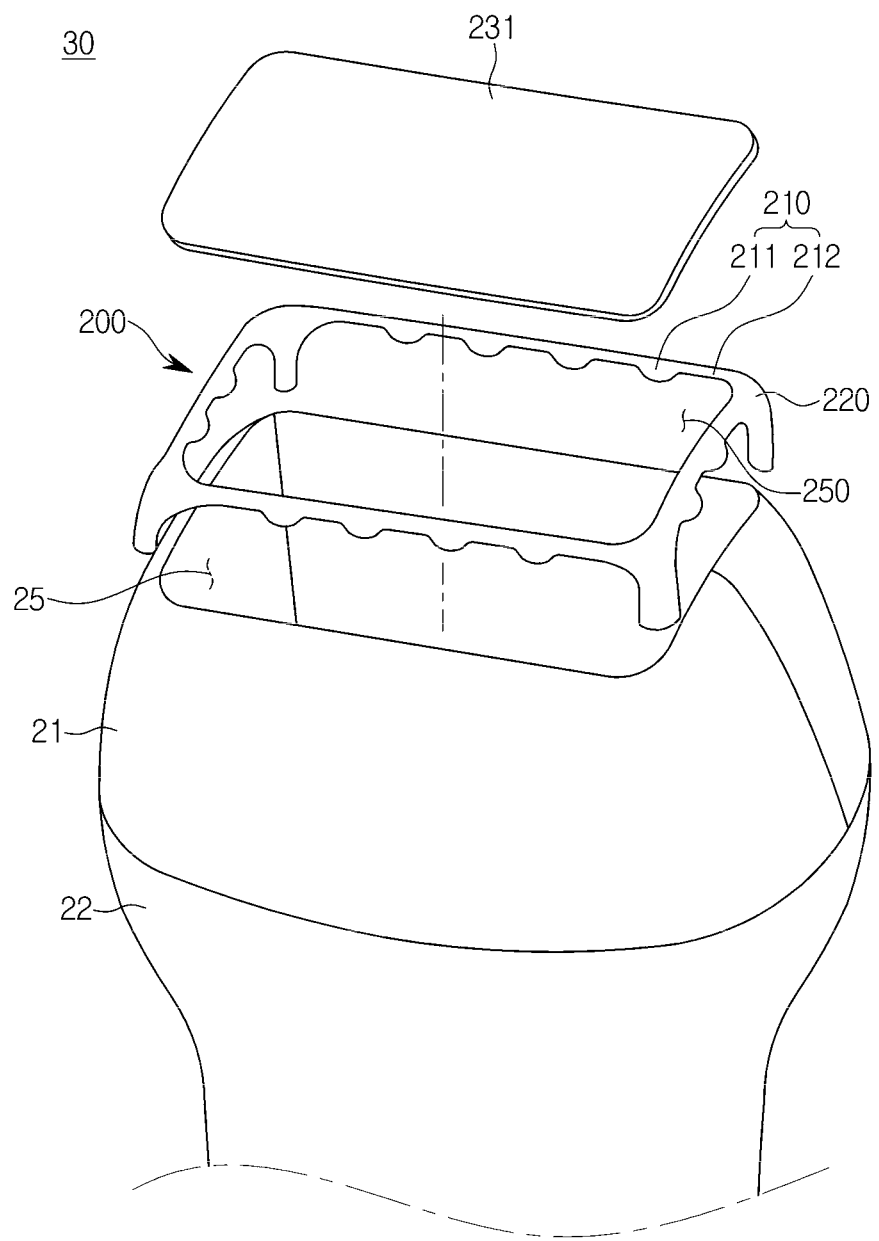
FIG. 6 is an exploded view of a lens and a buffer member in an ultrasonic probe according to another embodiment of the present disclosure.
Figure 7:
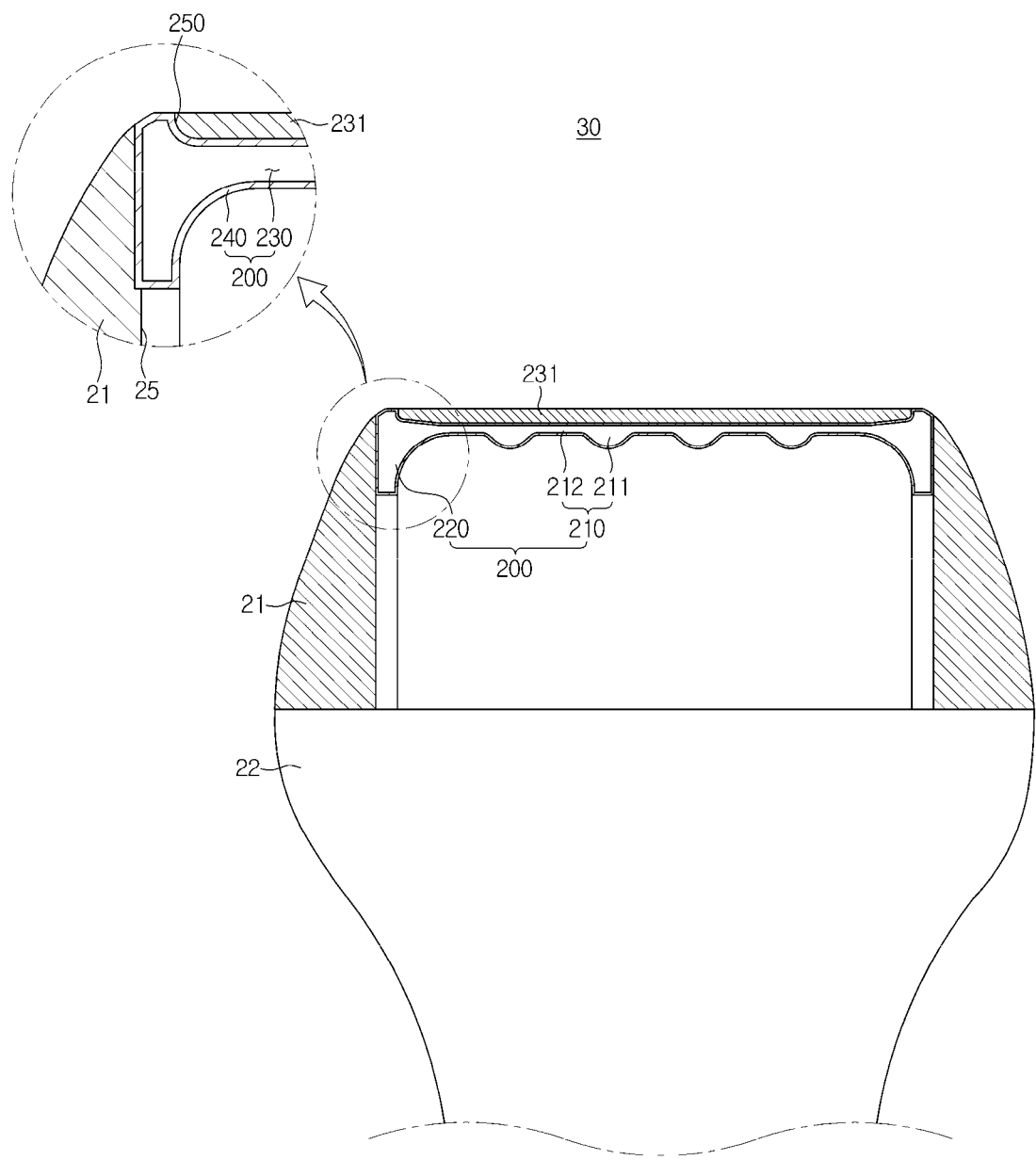
FIG. 7 is a cross-sectional view of the ultrasonic probe illustrated in FIG. 6.

FIG. 6 is an exploded view of a lens and a buffer member in an ultrasonic probe according to another embodiment of the present disclosure, and FIG. 7 is a cross-sectional view of the ultrasonic probe illustrated in FIG. 6.

As illustrated in FIGS. 6 and 7, an ultrasonic probe 30 according to another embodiment of the present disclosure may include almost the same configurations as the ultrasonic probe 20 (refer to FIG. 3) according to an embodiment of the present disclosure, but may be different from the ultrasonic probe 20 in the structure of a buffer member 200.

Hereinafter, the structure of the ultrasonic probe 30 according to another embodiment of the present disclosure will be described, focusing on the difference.

The ultrasonic probe 30 according to another embodiment of the present disclosure includes the buffer member 200 between the case 21 and the side surface of the transducer 23 (refer to FIG. 4), so that external impact applied to a front surface or side edges of the ultrasonic probe 30 may not be transmitted to the transducer 23 by the buffer member 200 or the external impact buffered by the buffer member 200 may be transmitted to the transducer 23.

That is, external impact may be first transmitted to the buffer member 200 and may be buffered in the buffer member 200, and then transmitted to the transducer 23. Therefore, by providing the buffer member 200, the transducer 23 may be prevented from being damaged by external impact.

The buffer member 200 may include a first buffer part 210 provided along the circumference of the transducer 23 and a second buffer part 220 provided on a portion of the first buffer part 210.

The first buffer part 210 may be looped to cover the entire side surfaces of the transducer 23. The second buffer part 220 may be disposed at a position where an edge of the first buffer part 210 meets. The second buffer part 220 may extend in a direction from the first buffer part 210 toward the handle 22.

The second buffer part 220 may be disposed in the rear of the first buffer part 210. A plurality of the second buffer parts 220 may be provided. In a case where the first buffer part 210 has a substantially rectangular ring shape, the second buffer parts 220 may be positioned at each corner of the first buffer part 210, but are not limited thereto.

The buffer member 200 may include a hole 250 through which the transducer 23 including the lens 231 passes. The lens 231 may be brought into contact with an external target object through the opening 25 of the case 21 and the hole 250 of the buffer member 200.

The buffer member 200 may include a buffer space 230 provided in the buffer member 200 and a buffer membrane 240 provided to cover the buffer space 230.

The buffer membrane 240 may firstly buffer external impact. The buffer space 230 may secondarily buffer the impact that has firstly been buffered by the buffer membrane 240.

The first buffer part 210 may include a first cushion portion 211 provided between the plurality of second buffer parts 220 and a first pressure portion 212 disposed adjacent to the first cushion portion 211.

The first cushion portion 211 may be disposed between the lens 231 and the handle 22. The volume of the first cushion portion 211 may be larger than the volume of the first buffer part 110 (refer to FIG. 5) according to an embodiment of the present disclosure.

The volume of the first pressure portion 212 may be smaller than the volume of the first buffer part 110 according to an embodiment of the present disclosure.

The volume of the first cushion portion 211 may be larger than the volume of the first pressure portion 212. The first pressure portion 212 may form a narrow passage. Accordingly, the first cushion portion 211 may perform a function of a cushion that may buffer external impact, and the cushioning function of the first cushion portion 211 may be further enhanced due to the difference in pressure by the first pressure portion 212.

A plurality of the first cushion portions 211 and a plurality of the first pressure portions 212 may be provided and the plurality of first cushion portions 211 and the plurality of first pressure portions 212 may be alternately arranged. That is, the plurality of first cushion portion 211 may be disposed between the plurality of first pressure portions 212, and the plurality of first pressure portion 212 may be disposed between the plurality of first cushion portions 211.

Figure 8:
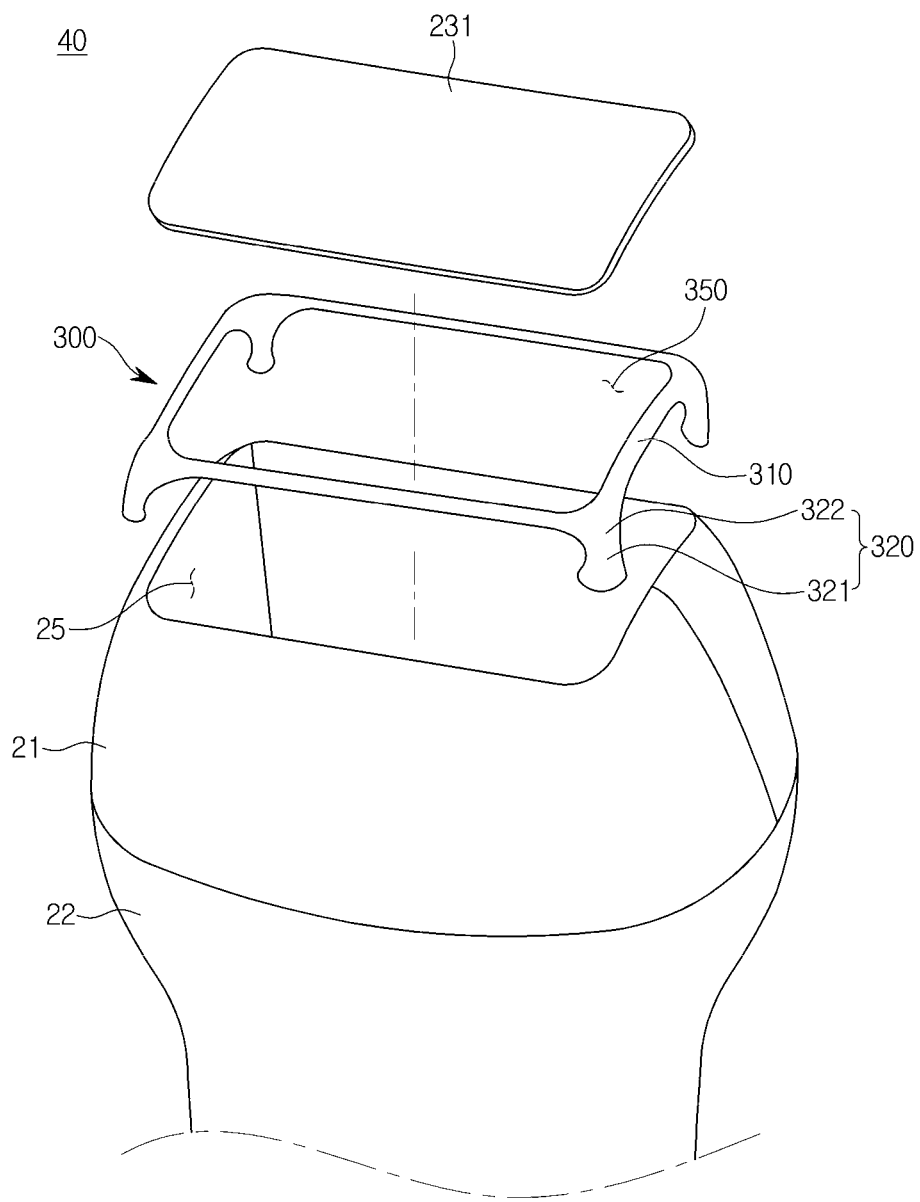
FIG. 8 is an exploded view of a lens and a buffer member in an ultrasonic probe according to another embodiment of the present disclosure.
Figure 9:
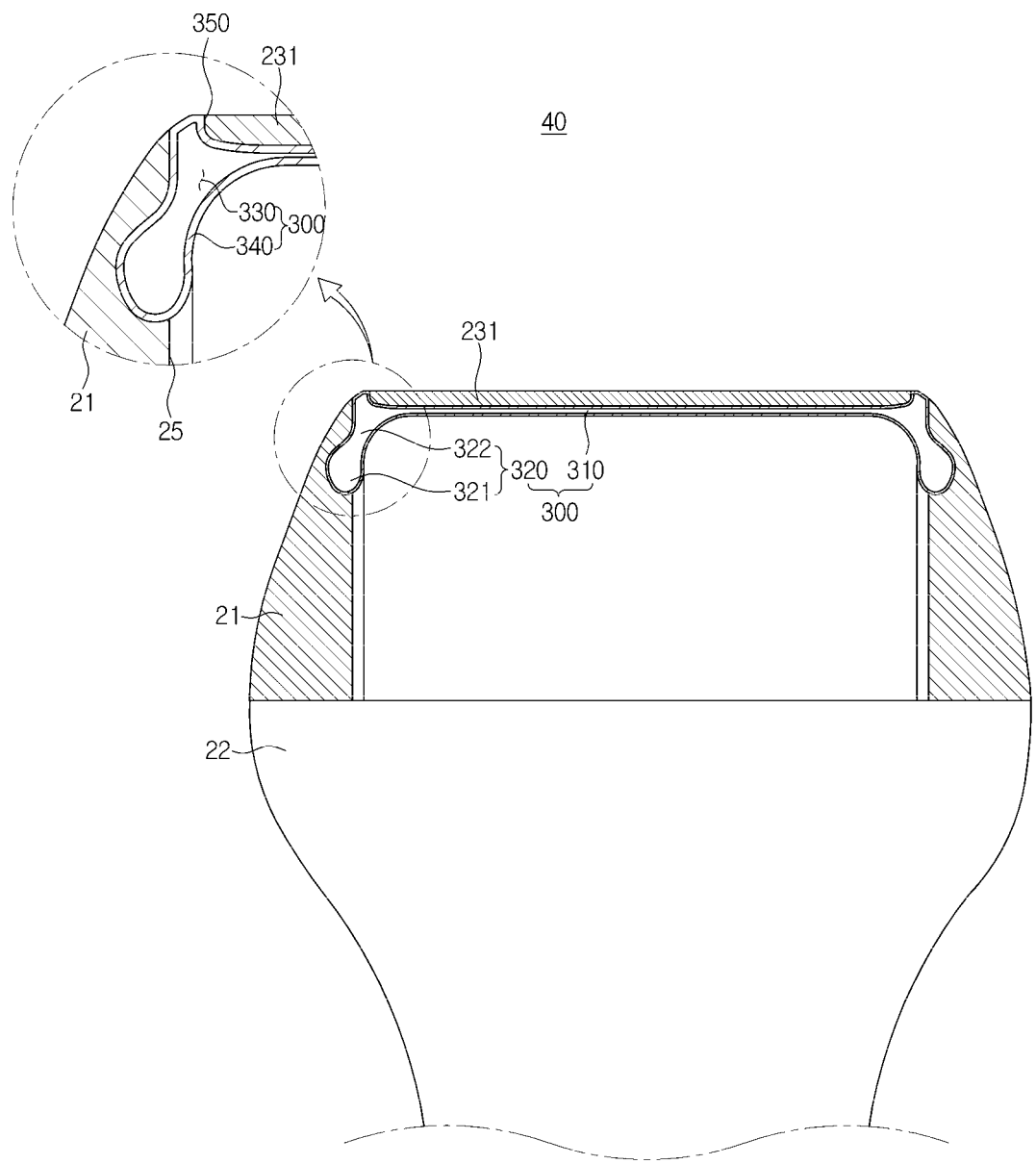
FIG. 9 is a cross-sectional view of the ultrasonic probe illustrated in FIG. 8.

FIG. 8 is an exploded view of a lens and a buffer member in an ultrasonic probe according to another embodiment of the present disclosure, and FIG. 9 is a cross-sectional view of the ultrasonic probe illustrated in FIG. 8.

As illustrated in FIGS. 8 and 9, an ultrasonic probe 40 according to another embodiment of the present disclosure may include almost the same configurations as the ultrasonic probe 20 (refer to FIG. 3) according to an embodiment of the present disclosure, but may be different from the ultrasonic probe 20 in the structure of a buffer member 300.

Hereinafter, the structure of the ultrasonic probe 40 according to another embodiment of the present disclosure will be described, focusing on the difference.

The ultrasonic probe 40 according to another embodiment of the present disclosure includes the buffer member 300 between the case 21 and the side surface of the transducer 23 (refer to FIG. 4), so that external impact applied to the front surface or the side edges of the ultrasonic probe 40 may not be transmitted to the transducer 23 by the buffer member 300 or the external impact buffered by the buffer member 300 may be transmitted to the transducer 23.

That is, external impact may be first transmitted to the buffer member 300 and may be buffered in the buffer member 300, and then transmitted to the transducer 23. Therefore, by providing the buffer member 300, the transducer 23 may be prevented from being damaged by external impact.

The buffer member 300 may include a first buffer part 310 provided along the circumference of the transducer 23 and a second buffer part 320 provided on a portion of the first buffer part 310.

The first buffer part 310 may be looped to cover the entire side surfaces of the transducer 23. The second buffer part 320 may be disposed at a position where an edge of the first buffer part 310 meets. The second buffer part 320 may extend in a direction from the first buffer part 310 toward the handle 22.

The second buffer part 320 may be disposed in the rear of the first buffer part 310. A plurality of the second buffer parts 320 may be provided. In a case where the first buffer part 310 has a substantially rectangular ring shape, the second buffer parts 320 may be positioned at each corner of the first buffer part 310, but are not limited thereto.

The buffer member 300 may include a hole 350 through which the transducer 23 including the lens 231 passes. The lens 231 may be brought into contact with an external target object through the opening 25 of the case 21 and the hole 350 of the buffer member 300.

The buffer member 300 may include a buffer space 330 provided in the buffer member 300 and a buffer membrane 340 provided to cover the buffer space 330.

The buffer membrane 340 may firstly buffer external impact. The buffer space 330 may secondarily buffer the impact that has firstly been buffered by the buffer membrane 340.

The second buffer part 320 may include a second cushion portion 321 provided between the first buffer parts 310 and a second pressure portion 322 disposed adjacent to the second cushion portion 321.

The second pressure portion 322 may be disposed between the first buffer part 310 and the second cushion portion 321. The volume of the second cushion portion 321 may be larger than the volume of the second buffer part 120 (refer to FIG. 5) according to an embodiment of the present disclosure.

The volume of the second pressure portion 322 may be smaller than the volume of the second buffer part 120 according to an embodiment of the present disclosure.

The volume of the second cushion portion 321 may be larger than the volume of the second pressure portion 322. The second pressure portion 322 may form a narrow passage. Accordingly, the second cushion portion 321 may perform a function of a cushion that may buffer external impact, and the cushioning function of the second cushion portion 321 may be further enhanced due to the difference in pressure by the second pressure portion 322.

The second cushion portion 321 may be positioned in the rear of the second pressure portion 322. A plurality of the second cushion portions 321 and a plurality of the second pressure portions 322 may be provided, but the present disclosure is not limited thereto.

Figure 10:
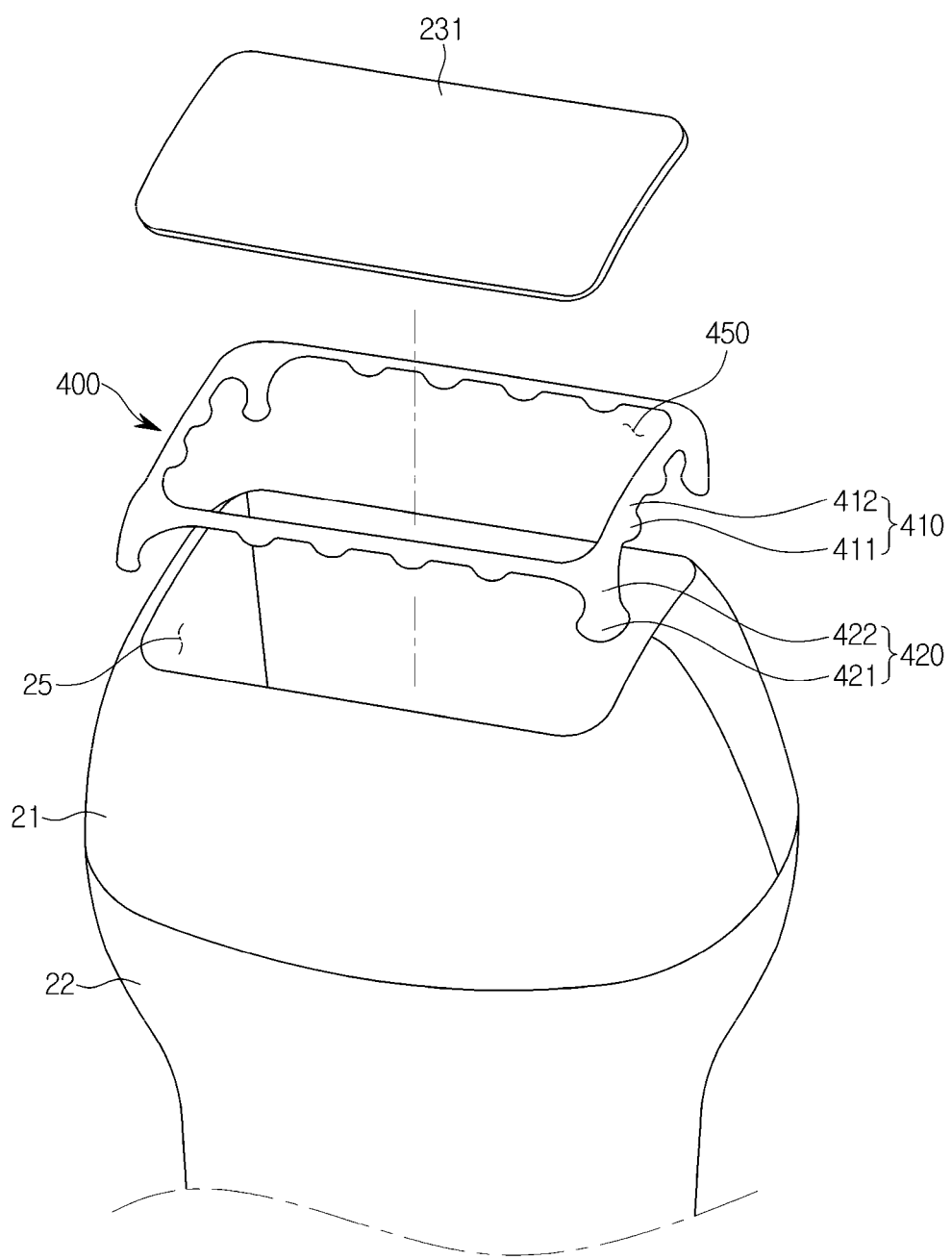
FIG. 10 is an exploded view of a lens and a buffer member in an ultrasonic probe according to another embodiment of the present disclosure.
Figure 11:
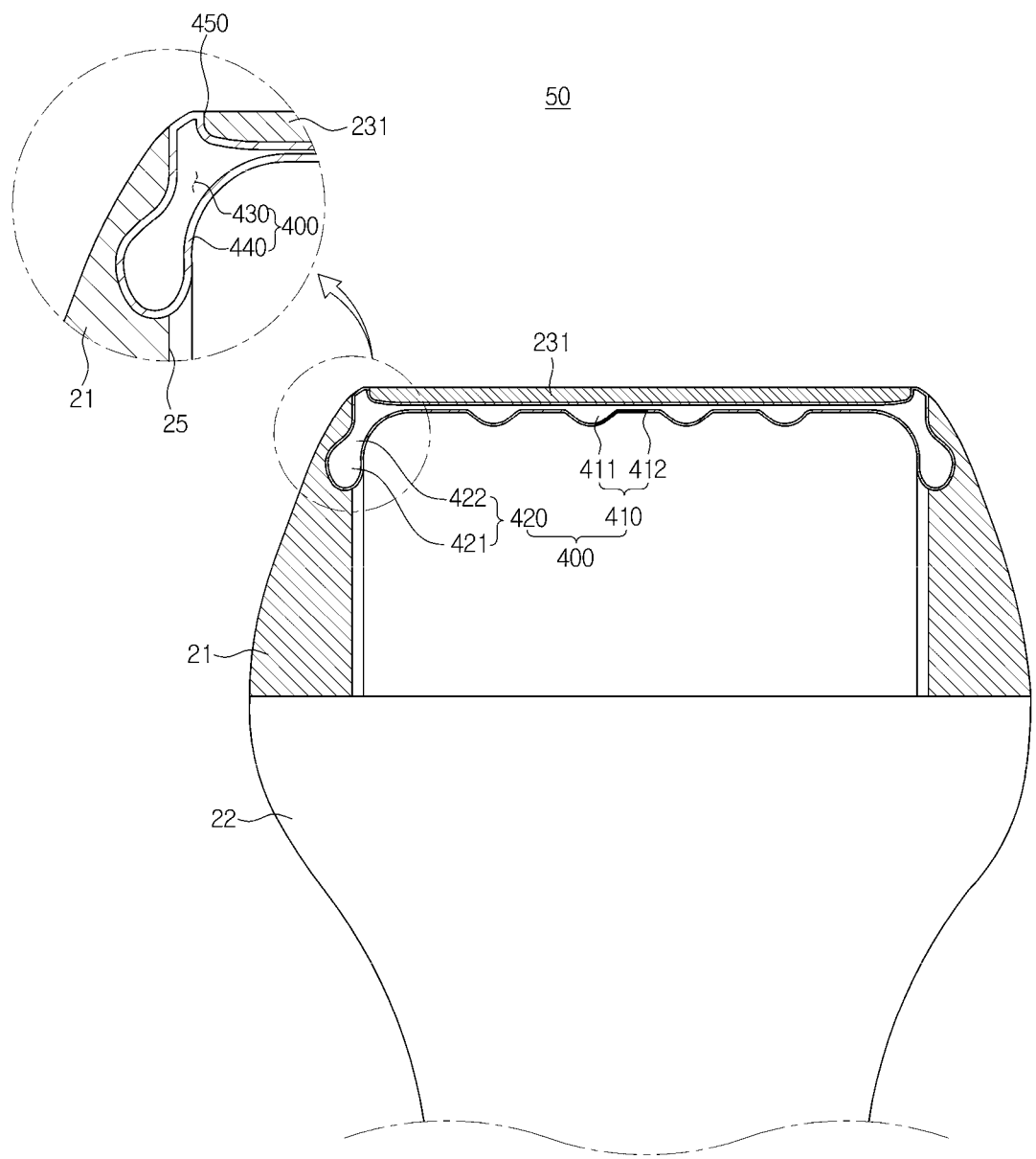
FIG. 11 is a cross-sectional view of the ultrasonic probe illustrated in FIG. 10.

FIG. 10 is an exploded view of a lens and a buffer member in an ultrasonic probe according to another embodiment of the present disclosure, and FIG. 11 is a cross-sectional view of the ultrasonic probe illustrated in FIG. 10.

As illustrated in FIGS. 10 and 11, an ultrasonic probe 50 according to another embodiment of the present disclosure may include almost the same configurations as the ultrasonic probe 20 (refer to FIG. 3) according to an embodiment of the present disclosure, but may be different from the ultrasonic probe 20 in the structure of a buffer member 400.

Hereinafter, the structure of the ultrasonic probe 50 according to another embodiment of the present disclosure will be described, focusing on the difference.

The ultrasonic probe 50 according to another embodiment of the present disclosure includes the buffer member 200 between the case 21 and the side surface of the transducer 23 (refer to FIG. 4), so that external impact applied to a front surface or side edges of the ultrasonic probe 50 may not be transmitted to the transducer 23 by the buffer member 400 or the external impact buffered by the buffer member 400 may be transmitted to the transducer 23.

That is, external impact may be first transmitted to the buffer member 400 and may be buffered in the buffer member 400, and then transmitted to the transducer 23. Therefore, by providing the buffer member 400, the transducer 23 may be prevented from being damaged by external impact.

The buffer member 400 may include a first buffer part 410 provided along the circumference of the transducer 23 and a second buffer part 420 provided on a portion of the first buffer part 410.

The first buffer part 410 may be looped to cover the entire side surfaces of the transducer 23. The second buffer part 420 may be disposed at a position where an edge of the first buffer part 410 meets. The second buffer part 420 may extend in a direction from the first buffer part 410 toward the handle 22.

The second buffer part 420 may be disposed in the rear of the first buffer part 410. A plurality of the second buffer parts 420 may be provided. In a case where the first buffer part 410 has a substantially rectangular ring shape, the second buffer parts 420 may be positioned at each corner of the first buffer part 410, but are not limited thereto.

The buffer member 400 may include a hole 450 through which the transducer 23 including the lens 231 passes. The lens 231 may be brought into contact with an external target object through the opening 25 of the case 21 and the hole 450 of the buffer member 400.

The buffer member 400 may include a buffer space 430 provided in the buffer member 400 and a buffer membrane 440 provided to cover the buffer space 430.

The buffer membrane 440 may firstly buffer external impact. The buffer space 430 may secondarily buffer the impact that has firstly been buffered by the buffer membrane 440.

The first buffer part 410 may include a first cushion portion 411 provided between the plurality of second buffer parts 420 and a first pressure portion 412 disposed adjacent to the first cushion portion 411.

The first cushion portion 411 may be disposed between the lens 231 and the handle 22. The volume of the first cushion portion 411 may be larger than the volume of the first buffer part 110 (refer to FIG. 5) according to an embodiment of the present disclosure.

The volume of the first pressure portion 412 may be smaller than the volume of the first buffer part 110 according to an embodiment of the present disclosure.

The volume of the first cushion portion 411 may be larger than the volume of the first pressure portion 412. The first pressure portion 412 may form a narrow passage. Accordingly, the first cushion portion 411 may perform a function of a cushion that may buffer external impact, and the cushioning function of the first cushion portion 411 may be further enhanced due to the difference in pressure by the first pressure portion 412.

A plurality of the first cushion portions 411 and a plurality of the first pressure portions 412 may be provided, and the plurality of first cushion portions 411 and the plurality of first pressure portions 412 may be alternately arranged. That is, the plurality of first cushion portions 411 may be disposed between the plurality of first pressure portions 412, and the plurality of first pressure portions 412 may be disposed between the plurality of first cushion portions 411.

The second buffer part 420 may include a second cushion portion 421 provided between the first buffer part 410 and the handle 22, and a second pressure portion 422 disposed adjacent to the second cushion portion 421.

The second pressure portion 422 may be disposed between the first buffer part 410 and the second cushion portion 421. The volume of the second cushion portion 421 may be larger than the volume of the second buffer part 120 (refer to FIG. 5) according to an embodiment of the present disclosure.

The volume of the second pressure portion 422 may be smaller than the volume of the second buffer part 120 according to an embodiment of the present disclosure.

The volume of the second cushion portion 421 may be larger than the volume of the second pressure portion 422. The second pressure portion 422 may form a narrow passage. Accordingly, the second cushion portion 421 may perform a function of a cushion that may buffer external impact, and the cushioning function of the first second cushion portion 421 may be further enhanced due to the difference in pressure by the second pressure portion 422.

The second cushion portion 421 may be positioned in the rear of the second pressure portion 422. A plurality of the second cushion portions 421 and a plurality of the second pressure portions 422 may be provided, but the present disclosure is not limited thereto.

Figure 12:
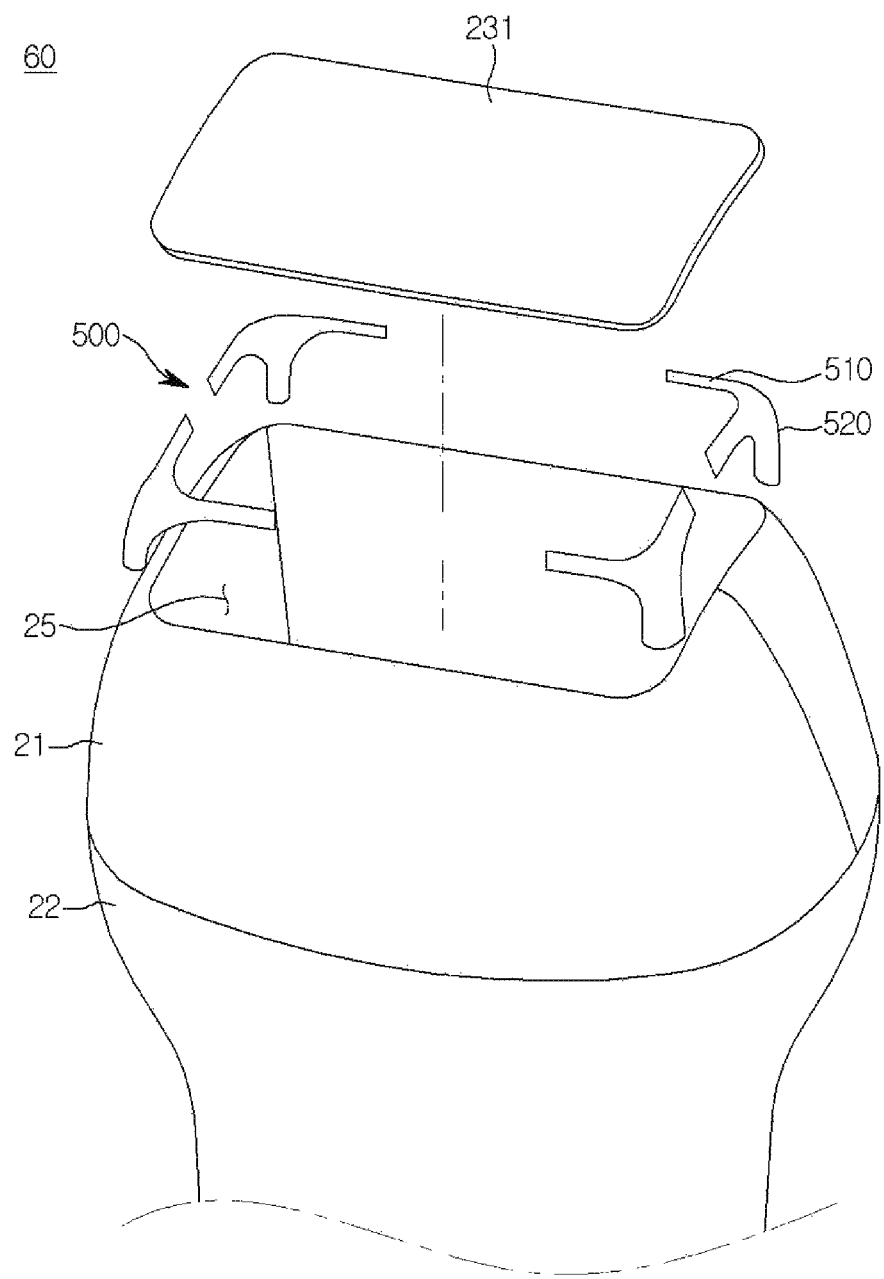
FIG. 12 is an exploded view of a lens and a buffer member in an ultrasonic probe according to another embodiment of the present disclosure.

FIG. 12 is an exploded view of a lens and a buffer member in an ultrasonic probe according to another embodiment of the present disclosure. As illustrated in FIG. 12, an ultrasonic probe 60 according to another embodiment of the present disclosure may include almost the same configurations as the ultrasonic probe 20 (refer to FIG. 3) according to an embodiment of the present disclosure, but may be different from the ultrasonic probe 20 in the structure of a buffer member 500.

Hereinafter, the structure of the ultrasonic probe 60 according to another embodiment of the present disclosure will be described, focusing on the difference.

The ultrasonic probe 60 may include the transducer 23 (see FIG. 4) that generates an ultrasonic signal and includes the lens 231 provided to transmit the ultrasonic signal to the outside. The lens 231 may focus the ultrasonic signal.

The ultrasonic probe 60 may include the case 21 that accommodates the transducer 23 and has the opening 25 at one side so that the lens 231 is brought into contact with an external target object, and the handle 22 mounted on the other side of the case 21.

The buffer member 500 capable of protecting the transducer 23 from external impact may be provided in the case 21. The buffer member 500 may be provided on one side of the transducer 23.

The buffer member 500 may be disposed between the case 21 and the transducer 23. The buffer member 500 may be provided along the circumference of the transducer 23. The buffer member 500 may be disposed to surround a side surface of the transducer 23. The buffer member 500 may be provided to cover the entirety of the side surfaces of the transducer 23.

Herein, the circumference of the transducer 23 refers to the rim or outer edge of the transducer 23 and may include a portion of the rim of the transducer 23 or the entire rim of the transducer 23.

The buffer member 500 according to another embodiment of the present disclosure may be disposed along at least a portion of the circumference of the transducer 23. A plurality of the buffer members 500 may be disposed apart from each other along the circumference of the transducer 23.

Four of the buffer members 500 may be disposed along the circumference of the transducer 23. Each of the buffer members 500 may be disposed at each corner along the circumference of the transducer 23, but is not limited thereto. For example, a large number of the buffer members 500 may be disposed at various positions within a range that may protect the transducer 23 from external impact.

The buffer member 500 may include a first buffer part 510 provided along the circumference of the transducer 23 and a second buffer part 520 provided on a portion of the first buffer part 510. The second buffer part 520 may be disposed at a position where an edge of the first buffer part 510 meets. The second buffer part 520 may extend in a direction from the first buffer part 510 toward the handle 22.

As is apparent from the above, the present disclosure can prevent the transducer from being damaged because the impact applied from the outside to the transducer can be buffered by disposing the buffer member around the transducer.

The present disclosure can prevent the quality of the ultrasound image from deteriorating due to external impact.

Although the technical idea of the present disclosure has been described above with reference to the specific embodiments, the scope of the present disclosure is not limited to these embodiments. It will be understood by those skilled in the art that changes may be made in these embodiments without departing from the principles and spirit of the disclosure in the scope of which is defined in the claims and their equivalents.

What is claimed is:

1. An ultrasonic probe comprising:
a transducer generating an ultrasonic signal and including a lens provided to transmit the ultrasonic signal to the outside;
a case accommodating the transducer and having an opening at one side so that the lens is configured to be brought into contact with an external target object; and
a buffer member provided along a circumference of the transducer to protect the transducer from external impact and disposed between the case and the transducer,
wherein the buffer member includes a buffer space provided inside the buffer member and along the circumference of the transducer to cover a side surface of the lens and a buffer membrane provided to cover the buffer space,
wherein the buffer membrane includes a first portion disposed between the buffer space and the case and a second portion disposed between the buffer space and the transducer,
wherein the buffer member includes a cushion portion provided along the circumference of the transducer and a pressure portion disposed adjacent to the cushion portion, a volume of the cushion portion being larger than a volume of the pressure portion, and
wherein the buffer member is filled with a fluid so that the fluid is movable through the cushion portion and the pressure portion.

2. The ultrasonic probe according to claim 1, wherein:
the transducer further includes a piezoelectric layer positioned adjacent to the lens and provided to generate the ultrasonic signal, and
the buffer member is disposed between the case and the piezoelectric layer.

3. The ultrasonic probe according to claim 2,
wherein the buffer member is provided along a circumference of the piezoelectric layer to cover the piezoelectric layer.

4. The ultrasonic probe according to claim 3,
wherein the buffer member is provided to cover entire side surfaces of the piezoelectric layer.

5. The ultrasonic probe according to claim 1,
wherein a hardness of the buffer member is lesser than a hardness of the case and greater than a hardness of the lens.

6. The ultrasonic probe according to claim 1,
wherein an elasticity of the buffer member is higher than an elasticity of the case.

7. The ultrasonic probe according to claim 1,
wherein the buffer member includes a first buffer part provided along the circumference of the transducer and a second buffer part provided on a portion of the first buffer part.

8. The ultrasonic probe according to claim 7, wherein:
a plurality of the second buffer parts are provided, and
the cushion portion is provided between the plurality of second buffer parts.

9. The ultrasonic probe according to claim 7, wherein:
the cushion portion is a first cushion portion and the pressure portion is a first pressure portion, and
the second buffer part includes a second cushion portion having a larger volume than a volume of the first buffer part, and a second pressure portion disposed between the first buffer part and the second cushion portion.

10. The ultrasonic probe according to claim 9,
wherein a volume of the second pressure portion is smaller than the volume of the second cushion portion.

11. The ultrasonic probe according to claim 1,
wherein the buffer space is filled with a material different from a material of the buffer membrane.

12. The ultrasonic probe according to claim 1, wherein:
the cushion portion is a first cushion portion and the pressure portion is a first pressure portion,
a plurality of the first cushion portions and a plurality of the first pressure portions are provided, and
the plurality of first cushion portions and the plurality of first pressure portions are alternately arranged.

13. The ultrasonic probe according to claim 1,
wherein the transducer is spaced apart from the buffer space.

14. An ultrasonic probe comprising:
a case;
a transducer accommodated inside the case, and including a piezoelectric layer for generating an ultrasonic signal and a lens disposed adjacent to the piezoelectric layer and provided to transmit the ultrasonic signal to the outside; and
a buffer member provided along a circumference of the piezoelectric layer to protect the piezoelectric layer from external impact and disposed between the case and the piezoelectric layer,
wherein the buffer member includes a buffer space provided inside the buffer member and along the circumference of the piezoelectric layer to cover a side surface of the lens and a buffer membrane provided to cover the buffer space,
wherein the buffer membrane includes a first portion disposed between the buffer space and the case and a second portion disposed between the buffer space and the piezoelectric layer,
wherein the buffer member includes a cushion portion provided along the circumference of the piezoelectric layer and a pressure portion disposed adjacent to the cushion portion, a volume of the cushion portion being larger that a volume of the pressure portion, and
wherein the buffer member is filled with a fluid so that the fluid is movable though the cushion portion and the pressure portion.

15. The ultrasonic probe according to claim 14, wherein the buffer member includes a first buffer part provided to cover entire side surfaces of the transducer and a second buffer part provided on a portion of the first buffer part.

16. The ultrasonic probe according to claim 14,
wherein the transducer is spaced apart from the buffer space.

17. An ultrasonic probe comprising:
a case;
a handle connected to one side of the case;
a transducer accommodated inside the case to generate an ultrasonic signal and including a lens provided to transmit the ultrasonic signal to the outside; and
a buffer member including a first buffer part provided along a side surface of the transducer to form a loop and a second buffer part disposed between the case and the transducer,
the second buffer part being provided on a portion of the first buffer part,
wherein the buffer member includes a buffer space provided inside the buffer member and along a circumference of the transducer to cover a side surface of the lens and a buffer membrane provided to cover the buffer space,
wherein the buffer membrane includes a first portion disposed between the buffer space and the case and a second portion disposed between the buffer space and the transducer,
wherein the first buffer part includes a cushion portion positioned between the lens and the handle, and a pressure portion disposed adjacent to the cushion portion and having a volume smaller than a volume of the cushion portion, and
wherein the buffer member is filled with a fluid so that the fluid is movable through the cushion portion and the pressure portion.

18. The ultrasonic probe according to claim 17, wherein the cushion portion is a first cushion portion and the pressure portion is a first pressure portion, and
the second buffer part includes a second cushion portion positioned between the first buffer part and the handle, and a second pressure portion disposed adjacent to the second cushion portion and having a volume smaller than a volume of the second cushion portion.

* * * * *